(12) United States Patent
Berrevoets et al.

(10) Patent No.: US 7,927,355 B2
(45) Date of Patent: Apr. 19, 2011

(54) CROSSLINK FOR SECURING SPINAL RODS

(75) Inventors: Gregory Berrevoets, Skandia, MI (US); Brian P. Janowski, Marquette, MI (US); Thomas S. Kilpela, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1200 days.

(21) Appl. No.: 11/408,629

(22) Filed: Apr. 21, 2006

(65) Prior Publication Data

US 2006/0271051 A1    Nov. 30, 2006

Related U.S. Application Data

(63) Continuation of application No. PCT/US2004/034897, filed on Oct. 21, 2004.

(51) Int. Cl.
*A61B 17/70* (2006.01)

(52) U.S. Cl. .......... 606/250; 606/253; 606/278

(58) Field of Classification Search .......... 606/60, 606/250–260, 278, 61, 246
See application file for complete search history.

(56) References Cited

U.S. PATENT DOCUMENTS

| | | | |
|---|---|---|---|
| 2,638,391 A | 5/1953 | Heusser | |
| 3,499,222 A | 3/1970 | Linkow et al. | |
| 4,611,582 A | 9/1986 | Duff | |
| 4,641,636 A | 2/1987 | Cotrel | |
| 4,773,402 A | 9/1988 | Asher et al. | |
| 4,957,495 A | 9/1990 | Kluger | |
| 5,002,542 A | 3/1991 | Frigg | |
| 5,005,562 A | 4/1991 | Cotrel | |
| 5,024,213 A | 6/1991 | Asher et al. | |
| 5,030,220 A | 7/1991 | Howland | |
| 5,084,049 A | 1/1992 | Asher et al. | |
| 5,102,412 A | 4/1992 | Rogozinski | |
| 5,129,900 A | 7/1992 | Asher et al. | |
| 5,133,716 A | 7/1992 | Plaza | |
| 5,147,359 A | 9/1992 | Cozad et al. | |

(Continued)

FOREIGN PATENT DOCUMENTS

EP   1093761   4/2001

(Continued)

OTHER PUBLICATIONS

PCT International Search Report mailed Oct. 14, 2005.

(Continued)

*Primary Examiner* — Eduardo C Robert
*Assistant Examiner* — Christina Negrelli
(74) *Attorney, Agent, or Firm* — Fitch, Even, Tabin & Flannery

(57) ABSTRACT

A crosslink member for securing spinal rods is disclosed having connector ends that include a brace and a locking member, each having an arcuate face resting on and securing a spinal rod. The locking member is secured by a cam member that rotates relative to the locking member and that cams against the connector to displace the cam member. The crosslink includes a male connector with a cylindrical cross rod received by a cavity in a female connector. The cross rod is secured by a pivotable clamp device in the female connector, and the cross rod connector and female connector may pivot, rotate, and telescope relative to each other. To reduce size without sacrificing pivot sweep, the cross rod has beveled edges, and the cavity of the female connector has windows to provide pivot clearance.

27 Claims, 8 Drawing Sheets

U.S. PATENT DOCUMENTS

| | | | |
|---|---|---|---|
| 5,154,718 A | 10/1992 | Cozad et al. |
| 5,176,680 A | 1/1993 | Vignaud et al. |
| 5,196,013 A | 3/1993 | Harms et al. |
| 5,275,600 A | 1/1994 | Allard et al. |
| 5,304,179 A | 4/1994 | Wagner |
| 5,312,405 A | 5/1994 | Korotko et al. |
| 5,330,473 A | 7/1994 | Howland |
| 5,334,203 A | 8/1994 | Wagner |
| 5,368,594 A | 11/1994 | Martin et al. |
| 5,403,316 A | 4/1995 | Ashman |
| 5,423,818 A | 6/1995 | Van Hoeck et al. |
| 5,439,463 A | 8/1995 | Lin |
| 5,443,465 A | 8/1995 | Pennig |
| 5,470,333 A | 11/1995 | Ray |
| 5,498,263 A | 3/1996 | DiNello et al. |
| 5,522,816 A | 6/1996 | DiNello et al. |
| 5,527,314 A | 6/1996 | Brumfield et al. |
| 5,531,745 A | 7/1996 | Ray |
| 5,531,747 A | 7/1996 | Ray |
| 5,545,167 A | 8/1996 | Lin |
| 5,569,246 A | 10/1996 | Ojima et al. |
| 5,584,831 A | 12/1996 | McKay |
| 5,601,552 A | 2/1997 | Cotrel |
| 5,609,592 A | 3/1997 | Brumfield et al. |
| 5,624,442 A | 4/1997 | Mellinger et al. |
| 5,630,816 A | 5/1997 | Kambin |
| 5,643,262 A | 7/1997 | Metz-Stavenhagen et al. |
| 5,662,653 A | 9/1997 | Songer et al. |
| 5,667,507 A | 9/1997 | Corin et al. |
| 5,683,393 A | 11/1997 | Ralph |
| 5,688,272 A | 11/1997 | Montague et al. |
| 5,707,372 A | 1/1998 | Errico et al. |
| 5,709,684 A | 1/1998 | Errico et al. |
| 5,709,685 A | 1/1998 | Dombrowski et al. |
| 5,810,819 A | 9/1998 | Errico et al. |
| 5,910,142 A | 6/1999 | Tatar |
| 5,928,232 A | 7/1999 | Howland et al. |
| 5,947,966 A | 9/1999 | Drewry et al. |
| 5,947,967 A | 9/1999 | Barker |
| 5,980,521 A | 11/1999 | Montague et al. |
| 5,980,523 A | 11/1999 | Jackson |
| 5,984,922 A | 11/1999 | McKay |
| 5,997,539 A | 12/1999 | Errico et al. |
| 6,063,089 A | 5/2000 | Errico et al. |
| 6,083,226 A | 7/2000 | Fiz |
| 6,096,039 A | 8/2000 | Stoltenberg et al. |
| 6,110,173 A | 8/2000 | Thomas, Jr. |
| 6,113,600 A | 9/2000 | Drummond et al. |
| 6,126,660 A | 10/2000 | Dietz |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,217,578 B1 | 4/2001 | Crozet et al. |
| 6,234,705 B1 | 5/2001 | Troxell |
| 6,238,396 B1 | 5/2001 | Lombardo |
| 6,261,288 B1 | 7/2001 | Jackson |
| 6,264,658 B1 | 7/2001 | Lee et al. |
| 6,283,967 B1 | 9/2001 | Troxell et al. |
| 6,302,882 B1 | 10/2001 | Lin et al. |
| 6,328,740 B1 | 12/2001 | Richelsoph |
| 6,402,751 B1 | 6/2002 | Hoeck et al. |
| 6,413,258 B1 | 7/2002 | Bernhardt, Jr. |
| 6,432,108 B1 | 8/2002 | Burgess et al. |
| 6,468,276 B1 | 10/2002 | McKay |
| 6,488,682 B2 | 12/2002 | Kikuchi et al. |
| 6,524,310 B1 | 2/2003 | Lombardo et al. |
| 6,554,832 B2 | 4/2003 | Shluzas |
| 6,602,253 B2 | 8/2003 | Richelsoph et al. |
| 6,692,500 B2 | 2/2004 | Reed |
| 6,866,664 B2 * | 3/2005 | Schar et al. .................. 606/252 |
| 6,887,241 B1 * | 5/2005 | McBride et al. ............ 606/86 A |
| 2002/0007183 A1 | 1/2002 | Lee et al. |
| 2002/0052603 A1 | 5/2002 | Nichols et al. |
| 2002/0111625 A1 | 8/2002 | Richelsoph et al. |
| 2002/0120272 A1 | 8/2002 | Yuan et al. |
| 2002/0143330 A1 | 10/2002 | Shluzas |
| 2002/0169448 A1 | 11/2002 | Vanacker |
| 2002/0169450 A1 | 11/2002 | Lange |
| 2002/0183749 A1 | 12/2002 | Burgess et al. |
| 2003/0018334 A1 | 1/2003 | Richelsoph et al. |
| 2003/0023244 A1 | 1/2003 | Richelsoph et al. |
| 2003/0050640 A1 | 3/2003 | Lee et al. |
| 2003/0114852 A1 | 6/2003 | Biedermann et al. |
| 2003/0114853 A1 | 6/2003 | Burgess et al. |
| 2004/0092931 A1 | 5/2004 | Taylor et al. |
| 2004/0116928 A1 | 6/2004 | Young et al. |
| 2005/0010222 A1 | 1/2005 | Cordaro |
| 2005/0080416 A1 | 4/2005 | Ryan et al. |
| 2005/0107789 A1 | 5/2005 | Sweeney |
| 2005/0113831 A1 | 5/2005 | Franck et al. |
| 2005/0228375 A1 | 10/2005 | Mazda et al. |
| 2005/0228377 A1 * | 10/2005 | Chao et al. ..................... 606/61 |
| 2006/0116687 A1 | 6/2006 | Miller et al. |
| 2006/0206114 A1 | 9/2006 | Ensign et al. |
| 2006/0271051 A1 | 11/2006 | Berrevoets et al. |
| 2008/0109039 A1 | 5/2008 | Michielli et al. |

FOREIGN PATENT DOCUMENTS

| | | |
|---|---|---|
| EP | 1138267 | 10/2001 |
| EP | 1302169 | 4/2003 |
| WO | 0217803 | 3/2002 |
| WO | 0230307 | 4/2002 |
| WO | 2006055914 A2 | 5/2006 |

OTHER PUBLICATIONS

Non-Final Rejection dated Jan. 19, 2007 from U.S. Appl. No. 10/692,460, filed Oct. 22, 2003.
Response dated Jul. 6, 2007 from U.S. Appl. No. 10/692,460, filed Oct. 22, 2003.
Non-Final Rejection dated Oct. 11, 2007 from U.S. Appl. No. 10/692,460, filed Oct. 22, 2003.
Response to Office Action dated Mar. 11, 2008 from U.S. Appl. No. 10/692,460, filed Oct. 22, 2003.
Non-Final Rejection dated Dec. 24, 2008 from U.S. Appl. No. 10/692,460, filed Oct. 22, 2003.
Amendment dated Apr. 24, 2009 from U.S. Appl. No. 10/692,460, filed Oct. 22, 2003.
Final Rejection dated Sep. 1, 2009 from U.S. Appl. No. 10/692,460, filed Oct. 22, 2003.
Amendment dated Nov. 24, 2009 from U.S. Appl. No. 10/692,460, filed Oct. 22, 2003.
Notice of Allowance dated Jan. 12, 2010 from U.S. Appl. No. 10/692,460, filed Oct. 22, 2003.
www.depuyacromed.com website printout for therapeutic products of DePuy AcroMed (14 pages), Copyright 2002.

* cited by examiner

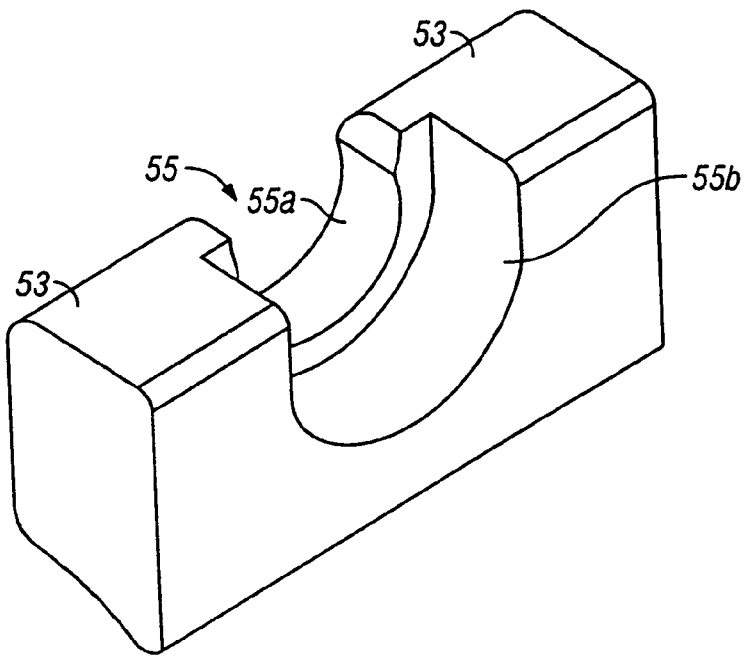
FIG. 5
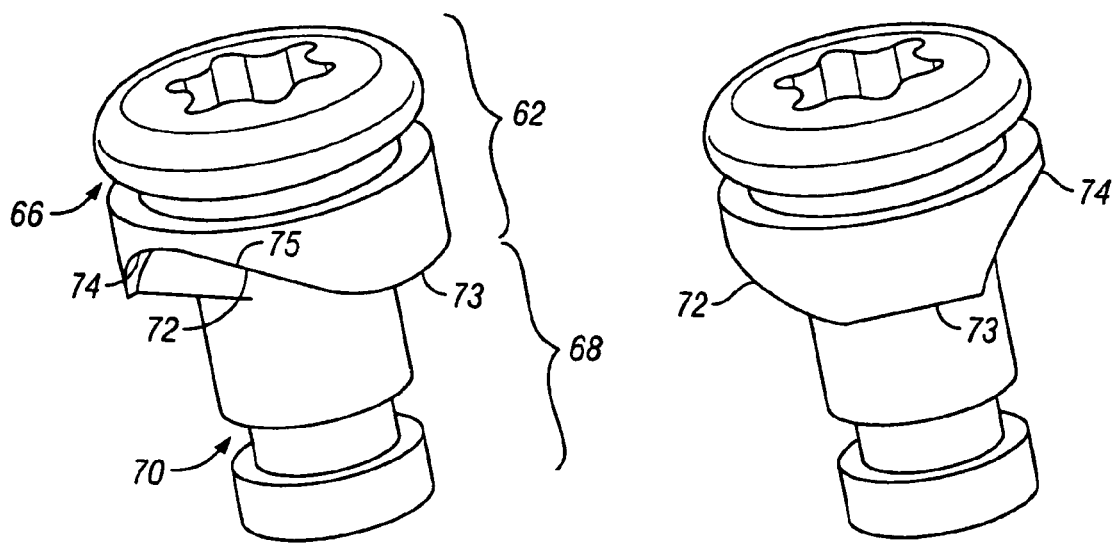
FIG. 6   FIG. 7

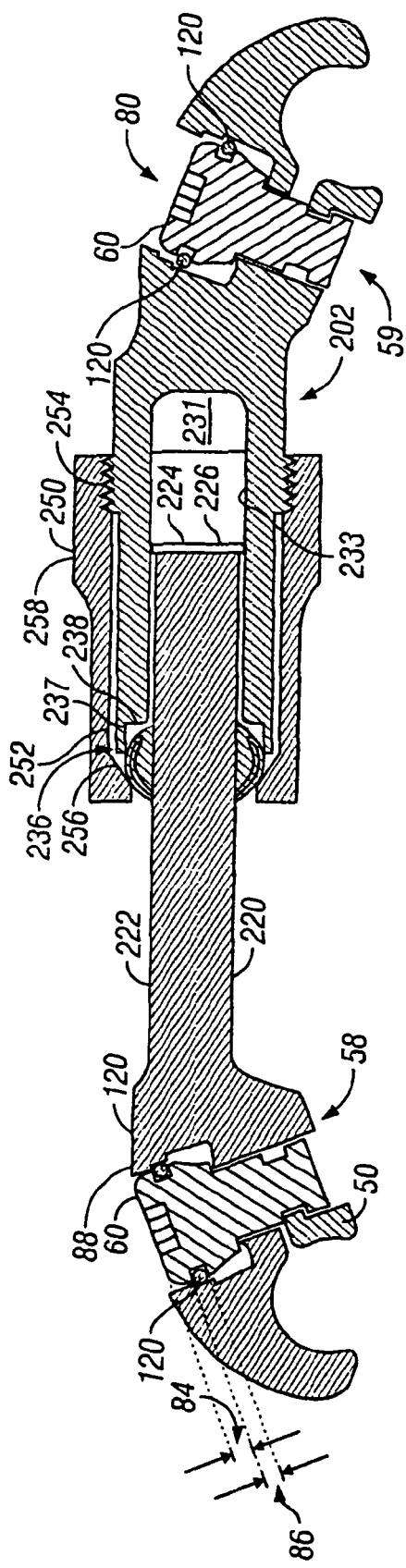
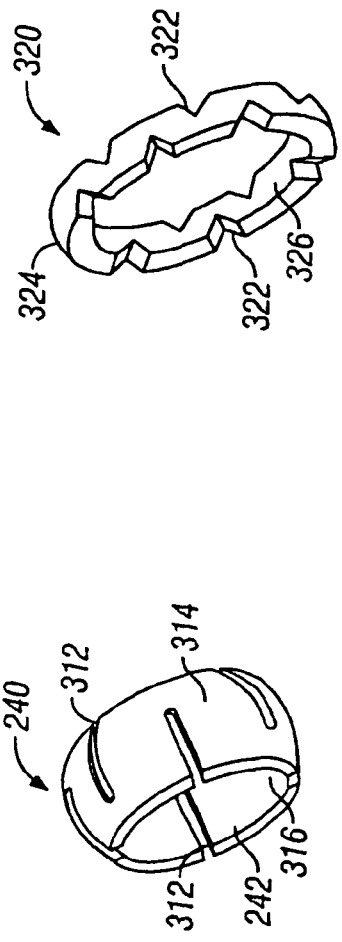
FIG. 8
FIG. 9
FIG. 10

CROSSLINK FOR SECURING SPINAL RODS

CROSS-REFERENCE TO RELATED APPLICATIONS

This application is a continuation of International application No. PCT/US2004/034897, filed Oct. 21, 2004, which is a continuation of U.S. patent application Ser. No. 10/692,460, filed Oct. 22, 2003, the contents of which are fully incorporated herein by reference.

FIELD OF THE INVENTION

The invention relates to a crosslink or connecting member to secure multiple spinal rods in relation to each other and, in particular, to a connecting member with a cam-locking mechanism for securing on multiple spinal rods.

BACKGROUND OF THE INVENTION

In surgical procedures involving the spine, it is common to secure a pair of spinal rods to a series of vertebrae. Furthermore, it is often necessary or desirable to secure the spinal rods relative to each other.

A spinal rod is often secured to the pedicle portion of a vertebrae by a screw. Surgical procedures involving the spine benefit from minimal invasiveness of the surgery from having a low-profile for any fixtures secured in the body. The ease of recovery and mobility of a patient with spinal fixtures is greatly influenced by the invasiveness of the procedure and by the size of any spinal fixtures.

When utilizing crosslinking or connecting members to secure pedicle screws, a number of obstacles are commonly encountered. Spinal rods are mounted by a surgeon in a custom-fit manner, including some bending of the rod, so that the rod is seated properly along the spine for holding the vertebral portions in proper relation. Accordingly, there is often not a predetermined distance between two spinal rods, and the rods may converge or diverge from each other. In addition, one spinal rod may have a portion directed at an angle different from that of the other rod. Therefore, the central axes of the two spinal rods are skewed or rotated relative to each other.

One attempt at overcoming these obstacles is a transverse connector system which includes two opposed connector ends for securing to spinal rods, with the connector ends secured to each other by a central fastening portion allowing three degrees of movement. That is, the central fastening portion allows the distance between the connector ends to be adjusted by compressing the system, to be pivoted relative to each other around a ball joint, and to be rotated relative to each other.

However, that approach included an internal cavity in one portion of the central fastening portion for receiving a cross rod of the other portion, such that the central fastening portion secures the two portions relative to each other. In such a design, the range of the pivoting movement permitted between the two portions is defined by the size of the internal cavity. In other words, the cross rod can only pivot to a position such that it abuts the wall of the internal cavity. In order to provide a greater sweep, the outer dimension and size of the entire portion must be increased.

Furthermore, it is common for the connecting ends of a connecting member to have a hook portion extending around a spinal rod and pointing back towards the center of the connecting member for securing to a spinal rod. In such an arrangement, installation or implantation of the device requires clearance laterally of the spinal rods so that the hook portion can be placed outside of the spinal rod and then drawn inward for securing on the rod. Often, the patient's soft tissue must be cleared for this purpose, a result which may exacerbate pain, discomfort, and healing time.

In addition, many connecting members utilize set screws. For instance, set screws may be utilized for securing the hook portion to the spinal rod, and a set screw maybe utilized for securing one connector end relative to the other. A set screw only provides a line or point contact with the surface against which it is driven. When a set screw drives against a spinal rod or other fixture, damage and distortion may occur at the interface. This can lead to uneven securement by the set screw, localized weakening of the fixture, loosening of the screw, or debris ground from either the screw or the fixture. Additionally, the screws require a threaded path long enough to provide a secure hold for the screw, which adds to the material cost, to the size of the fixture, and to the invasiveness of the procedure. Moreover, use of set screws often requires use of a torque driver to insure the screws are not over-tightened.

Moreover, the use of a set screw in the central fastening area presents a danger to the patient. The connecting member spans the dura portion of the spine. Put simply, portions of the spine other than bone, such as the discs or even the spinal cord itself, may be exposed. Utilization of a set screw in the central fastening area requires using a driver for securing the screw. Using such a driver exposes the non-bone spinal portions to damage caused by the driver slipping from the set screw and punching into the discs or spinal cord in, for instance, in awl-like fashion.

Accordingly, there has been a need for an improved crosslink member for securing spinal rods relative to each other.

SUMMARY OF THE INVENTION

In accordance with one aspect of the present invention, an improved crosslink connecting member for securing spinal rods to each other is disclosed. The crosslink has opposed connecting ends for securing the crosslink to the upper portion of a pair of spinal rods which are, in turn, secured to a patient's vertebrae, such as by pedicle screws. Each connector end has a central longitudinal axis and a curved end, in the form of a bracket or brace, which extends along the upper portion of the spinal rod, and partially around the lateral sides of the spinal rods. The curved end forms an arcuate inner surface for resting on and securing with the outer surface of the spinal rod. The arcuate inner surface extends orthogonally to the central longitudinal axis of the connector end or, alternatively, slightly back towards the opposing connector end. The curved end also forms an arcuate outer surface which curves around a portion of the spinal rod. The size and extension of the arcuate outer surface of the curved end is preferably shaped so that the wall thickness of the curved end is optimized to provide sufficient strength to the curved end while minimizing its size. Such a configuration minimizes the clearance required laterally, above, and below the spinal rods for seating the crosslink on the spinal rods.

In order to provide a secure hold to the spinal rod, each crosslink connector end has a locking member with an arcuate seating face. Once the crosslink connector ends are seated on the spinal rods, the locking members may be drawn into locking engagement with the spinal rods so that the arcuate seating face of the locking member and the arcuate inner surface of the connector end provide securement around a portion of the spinal rod. Preferably, the locking member and arcuate inner surface of the connector end provide surface contact encompassing a range of approximately 180 degrees ° to approximately 220° of the outer circumference of the rod. The range may or may not be continuous.

The locking member is secured to, preferably, a cam member. The locking member has a reciprocating motion provided by the cam member located in a cam bore. The cam member may be moved to and between locked position and an unlocked position. The cam member includes a cam surface providing the locked and unlocked positions and rotates against a pair of cam humps in the cam bore. As the cam member is rotated from the unlocked to the locked position, it translates upward. The cam member may be provided with a mating annular ring and annular groove, and the locking member has a bore with an open portion for receiving the cam member therein with a snap-fit. As the cam member rotates relative to the connector, its upward translation locks the locking member against the spine rod. Through the use of cam members and cam surfaces on the connector ends for securing to the spinal rods, problems attendant with using set screws against the spinal rods, as well as problems with over-torquing set screws, may be eliminated.

The connector end of the crosslink may rotated around the generally cylindrical spinal rod, and may be translated along the length of the spinal rod prior to securing the connector ends to the spinal rod. In accordance with a further aspect of the present invention, the crosslink provides three degrees of freedom or adjustment, in addition to the described rotational and translational adjustment between the connector end and the spinal rod. The crosslink includes a sleeve mechanism for securing the crosslink such that, after proper positioning and securement to the rod, further adjustment or movement is prevented. The distance between the two connector ends of the crosslink may be adjusted by compressing or extending the crosslink so that the crosslink may be properly sized to the distance between the spinal rods. For this, the crosslink includes a connector end with a cross rod that is inserted into a female connector end with a female receptacle or cavity, and the distance between the ends of the crosslink may be adjusted by moving the cross rod in or out of the female receptacle. Preferably, the cross rod is seated within a clamp device as part of the female connector that, prior to securing, allows the cross rod to move in or out of the female connector and clamp device.

For the second degree of adjustment, the connector ends of the crosslink may pivot relative to each other so that the crosslink may be secured to spinal rods that are converging or diverging in the region to which the crosslink is secured. As the cross rod is seated within the clamp device, this degree of adjustment is provided by pivoting the motion of the clamp device along with the cross rod within the female receptacle connector end. The clamp device may have a curved outer surface or otherwise provide sufficient clearance for pivotally mating with an internal surface of the female receptacle, or may have a pivot received by a pivot boss or bore in the female receptacle to allow the pivoting of the clamp device.

The third degree of adjustment allows the connector ends to rotate relative to each other. In one form, this is achieved by utilizing a cross rod that may rotate within the clamp device. Preferably, then, the cross rod has at least a portion that has a cylindrical outer surface, and the clamp device has a mating surface, such as cylindrically concave inner surface, against which the cross rod is seated. In another form, this is achieved by the cross rod being located within the clamp device wherein the clamp device itself may rotate within the female connector so that the cross rod and clamp device may rotate together.

In order to secure the cross rod within the female receptacle connector end, the clamp device is compressed or fastened against the cross rod, thereby securing the connector ends relative to each other. By securing the cross rod, and hence the connector ends, in this manner, set screws against the cross rod are avoided.

In order to compress or fasten the clamp against the cross rod, a generally cylindrical sleeve is provided. An outer surface of the female connector end includes threads, and an inner surface of the sleeve includes a portion with mating threads such that the sleeve moves along the female connector end when rotated. The sleeve is secured by rotating it around its central longitudinal axis which is coincident with the central longitudinal axis of the female connector end, thereby securing the connector ends relative to each other. The thread pitch is preferably selected so that a large number of rotations or revolutions of the sleeve are not required so that the crosslink apparatus can be quickly and easily secured.

The inner surface of the sleeve may also include a shoulder or chamfer. In some embodiments, movement of the sleeve towards a tightened position causes the shoulder or chamfer to contact the clamp device directly. In other embodiments, movement of the sleeve towards a tightened position causes the shoulder or chamfer to contact a deflectable portion of the female receptacle end, such as a flange, within which the clamp device is located. In either approach, the movement of the sleeve forces the shoulder or chamfer to compress the clamp device against the cross rod, thereby securing the connecting ends relative to each other. The outside of the sleeve may include features such as grooves, holes, or grips for finger tightening or for allowing a tool to grasp the surface. These features may be recessed from the outer surface of the sleeve to minimize the outer dimension of the sleeve. Drivers with sharp or pointed ends are not generally required. In addition, because the clamp device and sleeve do not grind into the rod, and because the clamping or compression force is provided by the shoulder of the sleeve, the use of a torque-limiting device can be avoided.

As mentioned above, the crosslink provides a degree of adjustment that allows the connector ends to pivot relative to each other. The female connector end receives the cross rod therein. The cross rod is allowed to move in a sweep pattern within the female connector end. In one aspect of the invention, the lateral sides of the cross rod are beveled to reduce the size of the cross rod in the lateral direction and to reduce the size of the female cavity needed to provide the required sweep. In another aspect, the cavity is open without side walls so that the size required for the female connector end is reduced, material is reduced, and clearance and footprint for the crosslink in the implantation site are reduced.

BRIEF DESCRIPTION OF THE DRAWINGS

In the drawings.

FIG. 5 is a perspective view of a locking member of the connector end of FIG. 4;

FIG. 6 is a first side plan view of a cam member of the connector end of FIG. 5;

FIG. 7 is a second side plan view of the cam member of FIG. 6;

FIG. 8 is a side elevation cross-sectional view of the embodiment of FIG. 1;

FIG. 9 is a perspective view of a first embodiment of a clamp device of the embodiment of FIG. 1;

FIG. 10 is a perspective view of a second embodiment of a clamp device of the embodiment of FIG. 1;

DESCRIPTION OF THE PREFERRED EMBODIMENTS

Figure 1:
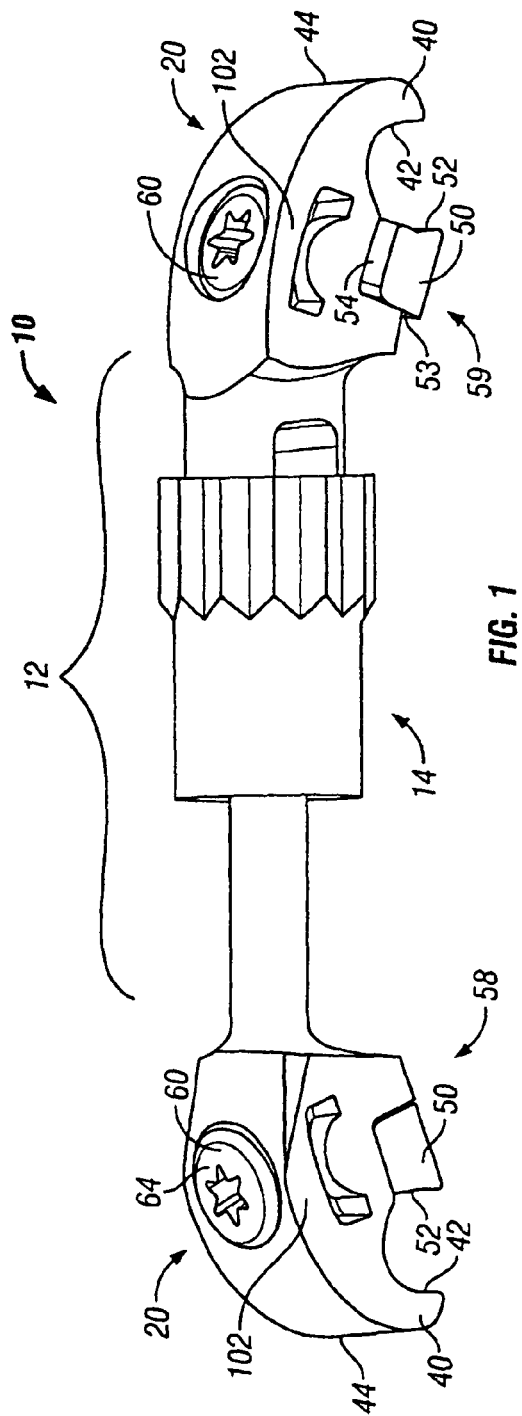
FIG. 1 is a perspective view of an embodiment of a crosslink connecting member of the present invention.
Figure 2:
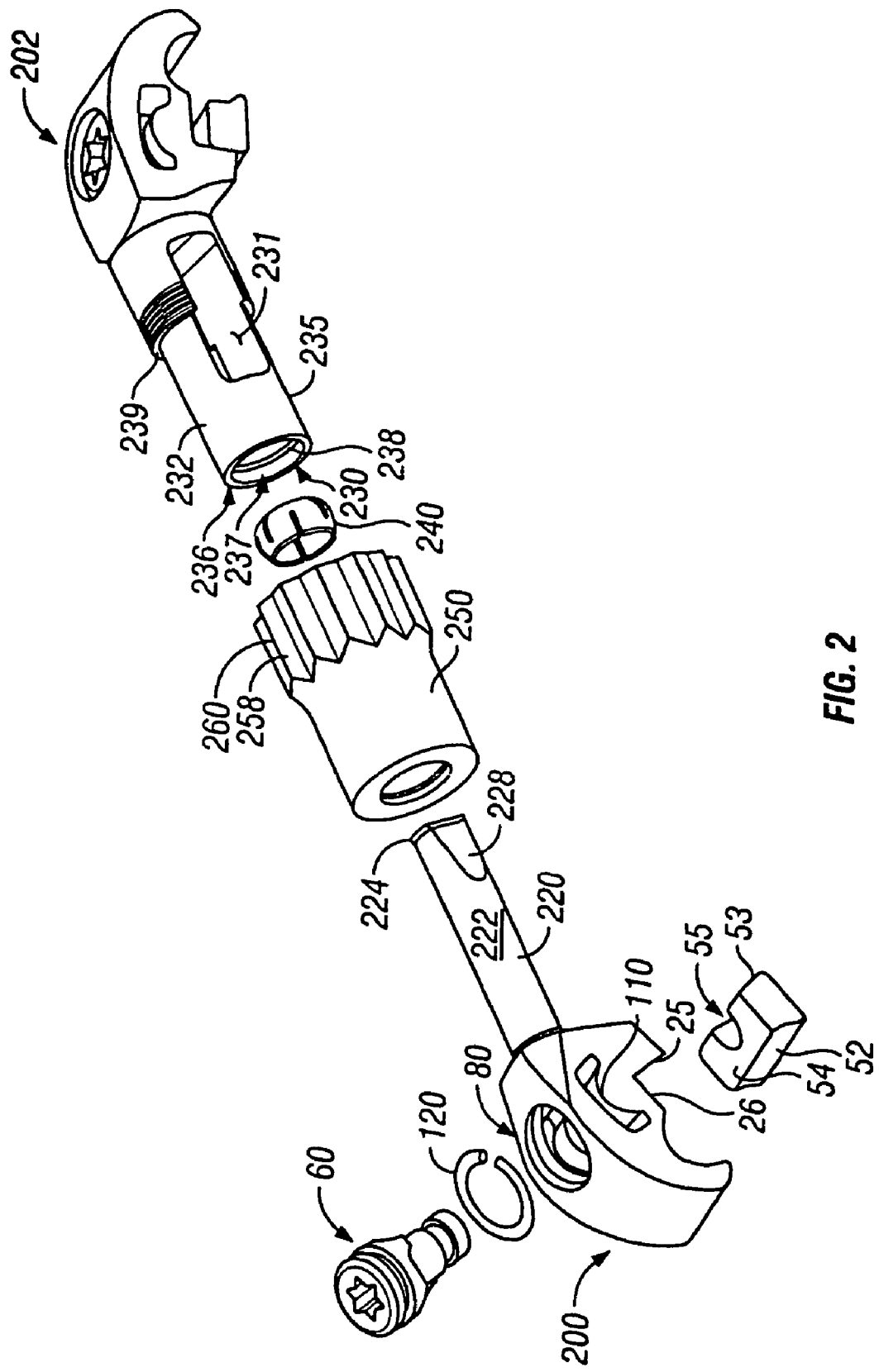
FIG. 2 is an exploded perspective view of the embodiment of FIG. 1.
Figure 3:
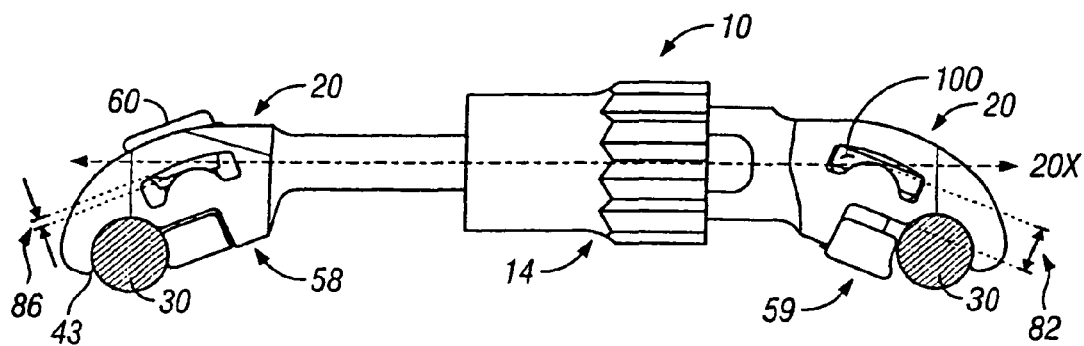
FIG. 3 is a side plan view of the embodiment of FIG. 1 seated on a pair of spinal rods.

Referring initially to FIGS. 1-3, a crosslink or connecting member 10 is depicted having two connecting ends or connectors 20 and a central span 12. In some embodiments, the central span 12 may simply be a rod or bar-like structure secured to or integral with the connectors 20. In other embodiments, the span may be a central connection portion 14 formed by the two connectors 20 with an ability to be adjusted, as will be discussed in greater detail below. In such a case, one connector 20 may be provided as a male connector or cross rod connector 200, and the other connector 20 may be provided as a rod receiving female connector 202, as will be discussed below. The preferred crosslink 10 may have an overall length, for instance, of 11 mm, 30 mm, 80 mm, or any length therebetween, and may have telescoping lengths covering the same range. However, many other lengths are possible including lengths outside this range.

The crosslink 10 spans between a pair of spinal rods 30 (see FIG. 3) to secure the spinal rods 30 relative to each other. The crosslink 10 is secured to each of the spinal rods 30 with one of the connectors 20. The connectors 20 each have a central longitudinal axis 20X, which may be coincident in embodiments where the central span 12 is a single, integral bar or rod-like structure. At one end of each connector 20, a curved end bracket or brace 40 is formed which contacts and secures against an outer cylindrical surface of a spinal rod 30. The brace 40 has a concave seating face 42 which is secured to the surface of the spinal rod 30. The seating face 42 extends to an outer distal end point 43. In one embodiment, the seating face 42 arcs such that a line tangential to the arc at the outer distal end point 43 may be drawn approximately orthogonal to the central longitudinal axis 20X of the connector 20. Alternatively, the seating face 42 may curve slightly more so as to actually curve around the spinal rod 30. If the seating face 42 curves slightly more in this manner, the crosslink 10 must be extended to be clear of the spinal rod 30 when mounting, and then compressed so that the spinal rod 30 rests flush against the seating face 42. The greater amount that the seating face 42 extends around the circumference of the spinal rod 30, the greater amount the crosslink 10 must be expanded or extended to be mounted on the spinal rod 30. As the crosslink 10 expands, additional clearance is required outside of the spinal rods 30 which enlarges the implantation site and may require moving more flesh of the patient. Therefore, it is preferred that the extent to which the seating face 42 extends around the lateral sides of the spinal rod 30 be minimized.

Similarly, the brace 40 has an outer arcuate surface 44. The brace 40 should provide sufficient strength for securing against the spinal rod 30, and the outer arcuate surface 44 should be shaped to allow for such strength while minimizing the clearance around the crosslink 10 required for implantation and securement. The wall thickness between the outer arcuate surface 44 and the arcuate seating face 42 is optimized to provide sufficient strength while minimizing its size and, therefore, the lateral clearance required for implanting the crosslink 10.

Preferably, the connector 20 contacts an area of the spinal rod 30 greater than 180° of the spinal rod 30, and most preferably approximately 220°. If contact through an arc of less than 180° is provided, the connector 10 may slip off the spinal rod 30. Therefore, each connector 20 further includes a locking member 50 with a concave seat 52, depicted in FIGS. 4 and 5. The locking member 50 may be moved between and to locked and unlocked positions, respectively depicted at 58 and 59 in FIG. 3. When in the locked position, the concave seat 52 of the locking member 50 and the seating face 42 of the brace 40 together secure the spinal rod 30 within the connector 20. The concave seat 52 of the locking member 50 and the seating face 42 provide surface contact which is greater and more secure than a line or point contact. Although the seating face 42 and locking member 50 may, alternatively, provide a three point contact for securing a spinal rod 30 within the connector 20, such is not preferable as the points may grind against the outer cylindrical surface of the spinal rod 30, and/or may deform the surface of the spinal rod 30 thereby causing loosening of the connector 20 from the spinal rod 30.

If the connector 20 contacts the spinal rod 30 at much greater than 220° of the outer circumference of the spinal rod 30, other problems may arise. As discussed above, if the brace 40 extends too far around the spinal rod 30, the crosslink would require excessive lateral clearance to mount on the spinal rod 30. Alternatively, the seating face 42 of the brace 40 may provide an extensive curve. If the seating face 42 has an extensive curve, problems arise in seating the connector 20 on the spinal rod 30. The connector 20 must be in the open or unlocked position 59 to secure the connector on the spinal rod 30. In other words, the locking member 50 must be positioned away from the connector 20 to allow the spinal rod 30 to pass into the concave seating face 42 of the brace 40. A greater length of arc provided in the concave seat 52 of the locking member 50 requires the brace 40 to be positioned further away from the connector 20. This results in needing clearance underneath the spinal rod, that is, between the spinal rod 30 and the vertebrae to which it is secured for the locking member 50 to extend. Accordingly, as the size of the curved end of the brace 40 is optimized for strength and size, the contact the locking member 50 and seating face 42 make with the spinal rod is optimized to provide a sufficient amount of contact with the outer circumference of the spinal rod 30 while minimizing the amount the brace 40 extends below the spinal rod 30.

As discussed above, the locking member 50 has locked and unlocked positions 58, 59. The movement of the locking member 50 to and between these positions is preferably provided by a rotating cam member 60, as depicted in FIGS. 6 and 7. The cam member 60 is located in a cam bore 80 within which the cam member 60 may reciprocate. Referring to FIGS. 6 and 7, the cam member 60 has a head 62 with a top surface 64 for receiving a driver (not shown) to turn the cam member 60 between the locked and unlocked positions 58, 59. The side of the head 62 may include an annular groove 66, which will be discussed later. Below the head 62 of the cam member 60 is a shank 68 with a recess in the form of an annular channel 70 formed therein.

Figure 4:
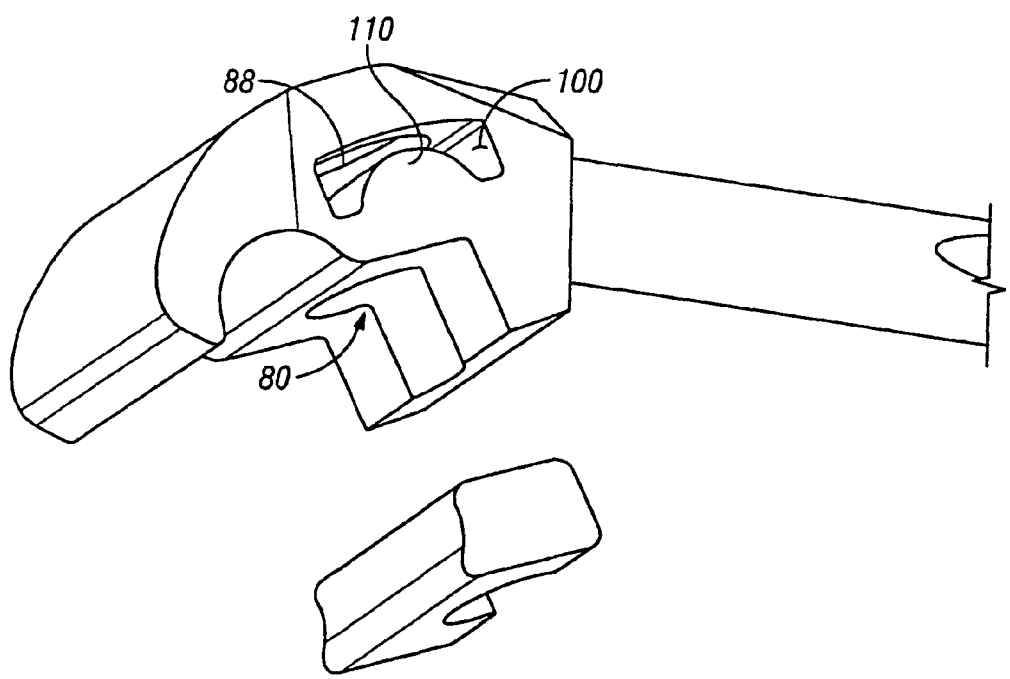
FIG. 4 is an exploded perspective view of a connector end of the embodiment of FIG. 1.

As can be seen in FIGS. 4 and 5, the locking member 50 has two generally flat inside surfaces 53, and a generally flat top surface 54. When the locking member 50 is in the locked position 58, the top surface 54 abuts a bottom surface 25 of the connector 20. As the locking member 50 moves to and between the locked and unlocked positions 58, 59, the inside surfaces 53 may abut and slide against a surface 26 of the connector 20. Additionally, a friction-inhibiting material (not shown) may be placed between the inside surfaces 53 of the locking member 50 and the abutting surface 26 of the connector 20. The two surfaces 53, 26 may also be provided with mating structure (not shown), such as a rail and guide (not shown), for directing and controlling the path of the moving locking member 50.

The locking member 50 is attached and secured to the cam member 60. Specifically, the locking member 50 has a C-shaped arcuate cut-out 55 defining an open portion 56 between the inside surfaces 53. The shank 68 of the cam member 60 is received within the cut-out 55 and is snap-fit therein. More specifically, an upper portion 55a of the cut-out 55 has a smaller inner diameter than the a lower portion 55b, and the upper portion 55a is received by the annular channel 70 of the shank 68 of the cam member 60. The cam member 60 may rotate relative to the locking member 50 as the narrow portion of the shank 68 at the annular channel 70 moves freely opposite the upper portion 55a of the cut-out 55. The cam member 60 translates along its central longitudinal axis upon rotation. As the cam member 60 moves up and down between the locked and unlocked positions 58, 59, the locking member 50 also moves up and down with the cam member 60. It should be noted that the recess in the form of an annular channel 70 need not be provided with a full rotation, instead only needing to provide a sufficient portion to support the locking member 50 its range of motion relative to the cam member 60.

Motion of the cam member 60 is provided by rotating the cam member 60 within the cam bore 80. Preferably, the cam member 60 is capable of rotating between 80-110° about its longitudinal axis between the locked and unlocked positions. Upon rotation of the cam member 60 from the unlocked position 59, cam surfaces of the cam member 60 and cam bore 80 of the connector 20 force the cam member 60 upward. Specifically, the cam member 60 has a cam surface 72 facing downward and located on the head 62 of the cam member 60. In the present embodiment, the cam surface 72 provides locked and unlocked positions 73, 74 and a transition area 75 therebetween.

Referring to FIGS. 3 and 8, the connector 20 may include a window 100 cut transversely through the connector 20 and through the cam bore 80. The window 100 includes a pair of elevated cam surfaces in the form of humps 110 located to the sides of the longitudinal axis 20X of the connector 20 and in the center of the window 100. Alternatively, the cam surfaces of the window 100 may be formed as elevated portions in another portion of the cam bore 80, such as at the edges of the windows 100. A lower portion 82 of the cam bore 80 below the window 100 (see FIG. 3) is sized generally to allow the shank 68 of the cam member 60 to pass therethrough while preventing the head 62 of the cam member 60 from doing so. The cam bore 80 has a top portion 84 above the window 100 (see FIG. 8) sized to permit the head 62 of the cam member 60 to be located therein such that the head 62 may move up and down within the cam bore 80. To provide the preferred geometry for the locking member 50 to secure to the spinal rod 30 and for the internal structure of the cam bore 80, the cam bore 80 is oriented such that its central longitudinal axis is oriented toward the center of the crosslink 10 at an angle from the top to bottom of the crosslink 10. Such an orientation of the cam bore 80 provides a low profile or height for the crosslink 10. Above each window 100 and lateral to the cam bore 80 are struts 102 further providing for a low-profile crosslink 10. The struts 102 provide strength to the connectors 20 and allow for stress to be distributed from one connector 20 to the other connector 20. Furthermore, they provide for a spring retention member in the form of a split ring 120, as will be discussed below, and the cam action of the cam bore 80, as will also be discussed below.

When the cam member 60 is assembled within the cam bore 80, the cam member 60 cannot pass through the lower portion 82 of the cam bore 80. The cam surface 72 of the cam member 60 rests, in the unlocked position 74, against the humps 110. As the cam member 60 rotates, the cam surface 72 moves across the humps 110. This movement causes the cam member 60 to rise through the cam bore 80 until the humps 110 reach the locked position 73 on the cam surface 72 of the cam member 60. The cam member 60 may continue to be rotated a small amount so that the humps 110 engage the flat of the locked position 73. In this manner, a driver (not shown) may be utilized for turning the cam member 60, a torque-limiting tool is unnecessary, and set screws directed against the spinal rod are eliminated. The locked position 73 may include a flat or a recess onto which the cam surface 72 of the cam member 60 may rotate to prevent the cam member 60 from unlocking.

During implantation and prior to securing the connectors 20 of the crosslink 10, the locking members 50 are held in the open or unlocked position 59. In order to achieve this, the annular groove 66 of the cam member head 62 is provided with a spring retention member in the form of, for instance, a split ring 120, and the cam bore 80 is provided with an intermediate portion 86 directly below and forming a shoulder 88 with the top portion 84 (see FIGS. 3, 8). Alternatively, the intermediate portion 86 can have an inner diameter that tapers inward from the window 100 to the shoulder 88. When initially in the unlocked position 59, the split ring 120 around the cam member 60 is located below the shoulder 88, such as in the window 100. Therefore, when the cam member 60 is rotated so that the humps 110 force the cam member 60 upwards, the split ring 120 is compressed and either forced from the window 100 into the intermediate portion 86 or from a lower, wider point of the intermediate portion 86 to an upper, smaller point of the intermediate portion 86. Accordingly, the split ring 120 holds the cam member 60, locking member 50, and connector 20 in an open, unlocked position 59 until the cam member 60 is specifically rotated, whereupon the split ring 120 compresses and allows the cam member 60 and locking member 50 to move to the locked position 58. By keeping the locking members 50 in an open position during implantation, positioning and implantation of the crosslink 10 is simplified for a surgeon.

Figure 16:
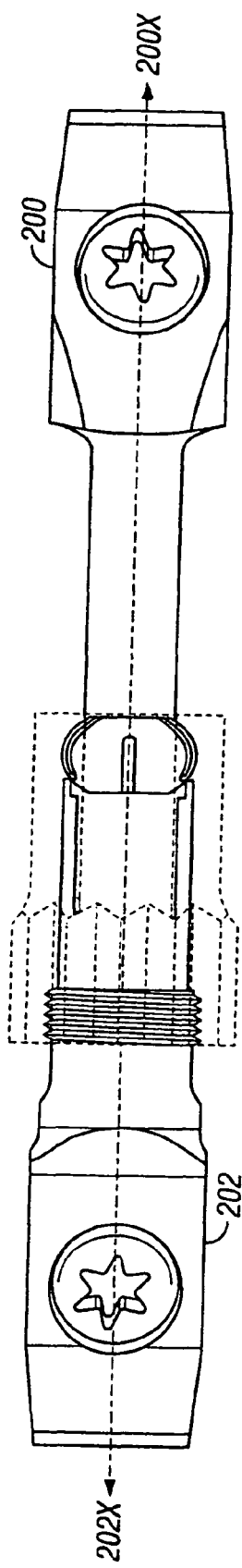
FIG. 16 is a top plan view of a crosslink member in an unpivoted position.
Figure 17:
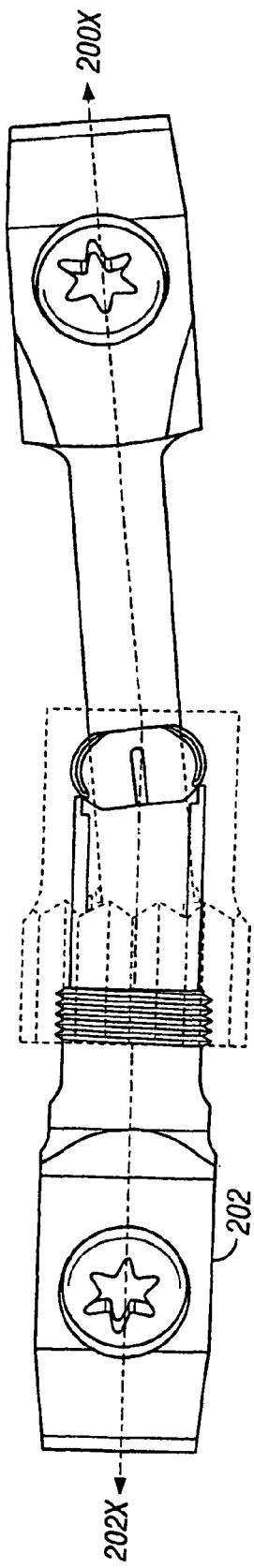
FIG. 17 is a top plan view of the crosslink member of FIG. 16 in a pivoted position.

As briefly discussed above, in embodiments where the central span 12 includes a central connection portion 14, the connectors 20 may include a male connector or cross rod connector 200, and a female connector 202 having central longitudinal axes 200X, 202X, respectively (see FIGS. 16 and 17). Referring to FIGS. 2 and 8, the cross rod connector 200 includes a cross rod 220 integral with the connector 200 and having an outer surface 222 at least a portion of which is cylindrical. The female connector 202 includes a cavity 230 along its central longitudinal axis 202X for receiving the cross rod 220. Between the cavity 230 and the cross rod 220 is a clamp device 240. The cross rod 220 is inserted into clamp device 240 and the cavity 230 and is clamped therein when the crosslink 10 is secured. The clamp device 240 has an inner surface 242 with at least a portion having an arcuate surface for mating with the cylindrical surface 222 of the cross rod 220.

The female connector 202 includes an outer surface 232 with a threaded portion 234, and a portion 235 without threads such that a shoulder 239 is formed between the portions 234, 235. The connection portion 14 includes a sleeve 250 having an inner surface 252 with internal threads 254 that mate with the threaded portion 234 of the female connector 202 such that the sleeve 250 secures to the female connector 202 by rotating around the central longitudinal axis 202X of the female connector 202, the axis 202X being coincident with a central longitudinal axis of the clamp device 240. The mating threaded portion 234 of the female connector 202 and threads 254 of the sleeve 250 are provided with a pitch selected so that a large number of revolutions of the sleeve 250 are not required so that the central connection portion 14 may be quickly and easily secured. As an alternative, the outer surface 232 of the female connector 202 and the inner surface 252 of the sleeve 250 maybe provided with connection means other than thread, such as the providing mating parts of a BNC connector, for example.

As the sleeve 250 tightens on the female connector 202, it causes compression on the clamp device 240 to secure the clamp device 240 on the cross rod 220. The inner surface 252 of the sleeve 250 further includes a shoulder 256 which may be radiused, or formed as either a chamfer or an edge. In one embodiment, the sleeve 250 tightens and, the shoulder 256 contacts the clamp device 240 directly (see e.g. FIGS. 2 and 8). In an alternate form of the invention, the shoulder 256 contacts a deflectable portion of the female connector (see, e.g., FIGS. 11 and 12), and the deflectable portion may have a chamfer. The shoulder 256 or chamfer causes the clamp device 240 to be compressed to secure the cross rod 220 therein.

The sleeve 250 has an outer surface 258, which may be provided with a portion having structure 260 for gripping and rotating the sleeve 250. The structure 260 may be gripping structure to allow a surgeon to finger-tighten the sleeve 250, may be structure to allow a wrench or other tool to grasp the outer surface 258 to rotationally tighten the sleeve 250, or a combination of both. Because the sleeve 250 is secured in this fashion, problems attendant with drivers with sharp or pointed ends are eliminated, and torque-limiting tools are not required. The shoulder 239 on the female connector 202 may also be utilized as a stop to prevent over-tightening of the sleeve 250 thereon.

When the crosslink 10 is being seated and secured to the spinal rods 30 by a surgeon, the cross rod connector 200 and the female connector 202 are preferably not secured. That is, the connectors 200, 202 are free to be manipulated relative to each other to allow the surgeon to properly seat the connectors 200, 202 on the spinal rods prior to securing the connection portion 14. When the connectors 200, 202 are not secured, it is preferred that they remain together so that the crosslink 10 can be a single apparatus that need not be assembled while in the vicinity of the implantation site. Accordingly, the cross rod 220 may include a lip or ridge 224 on its terminal end 226. The ridge 224 is inserted within the clamp device 240, and the clamp device 240 retains the ridge 224 therein. In some embodiments, the clamp device 240 may expand slightly to allow the ridge 224 to pass through, or the clamp device 240 may have an opening 244 (see FIGS. 11-15) such that the cross rod connector 200 is rotated to align the ridge 224 with the opening 244, the cross rod 220 is then inserted through the clamp device 240, and the cross rod connector 200 is then rotated so that the ridge 224 is no longer aligned with the opening 244.

In the embodiments of the invention depicted in FIGS. 2 and 8, the clamp device 240 is received by a circular terminal end 236 of the cavity 230 of the female connector 202. The clamp device 240 is held by the terminal end 236 of the cavity 230. The cavity 230 includes an inner surface 237 having a shoulder 238 against which an outer surface 314 of the clamp device 240 may slide. When the sleeve 250 is tightened, the clamp device 240 is compressed between the terminal end 236 of the cavity 230 and the shoulder 256 of the sleeve 250.

As depicted in FIGS. 2, 8, and 9, the clamp device 240 is preferably a ring-like clamp with alternating cut-outs 312. The cut-outs 312 allow the shape of the clamp 240 to be deflected inward when clamped or deflected outward when the ridge 224 of the cross rod 220 is inserted. The clamp 240 has an outer curved surface 314 so that the clamp 240 remains in contact with and is positioned by the circular terminal end 236 of the cavity 230 when the clamp 240 is pivoted. The clamp 240 has an inner cylindrical surface 316 for mating with the outer cylindrical surface 222 of the cross rod 220. An alternative clamp device 320 is depicted in FIG. 10, also being a ring-like clamp with alternating cut-outs 322, an outer curved surface 324, and an inner cylindrical surface 326. In one form of the invention, the shoulder 238 of the female connector 202 is positioned such that the clamp device 240, 320 may be contacted directly by the shoulder 256 of the sleeve 250. In other forms, the terminal end 236 of the female connector 230 may include deflectable portions (not shown) such as tabs (not shown) formed by longitudinal slits or cut-outs (not shown) such that the shoulder 256 of the sleeve 250 contacts the deflectable portions, thereby clamping the clamp device 240.

Figure 12:
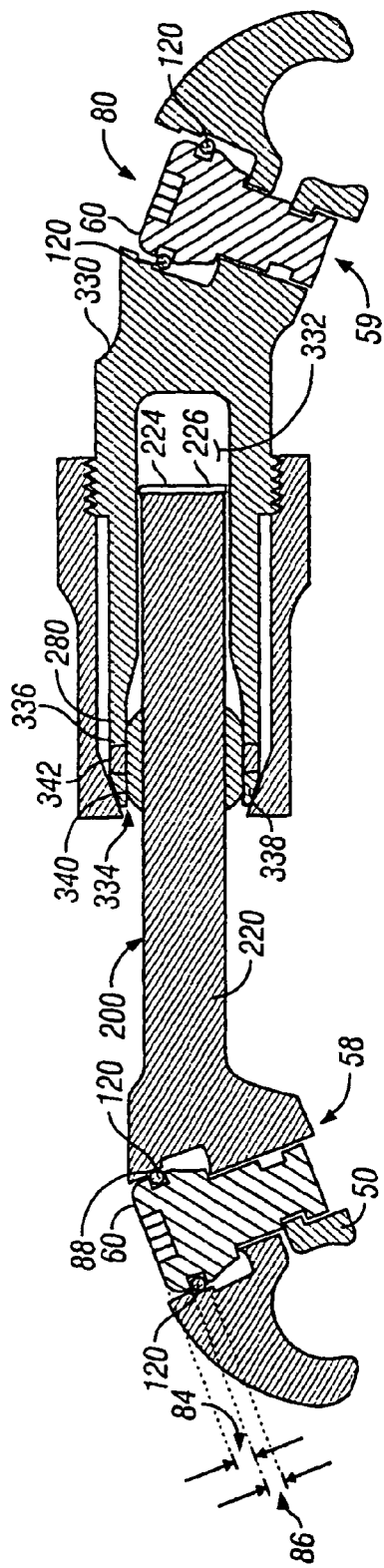
FIG. 12 is a side elevation cross-sectional view of the embodiment of FIG. 11.
Figure 11:
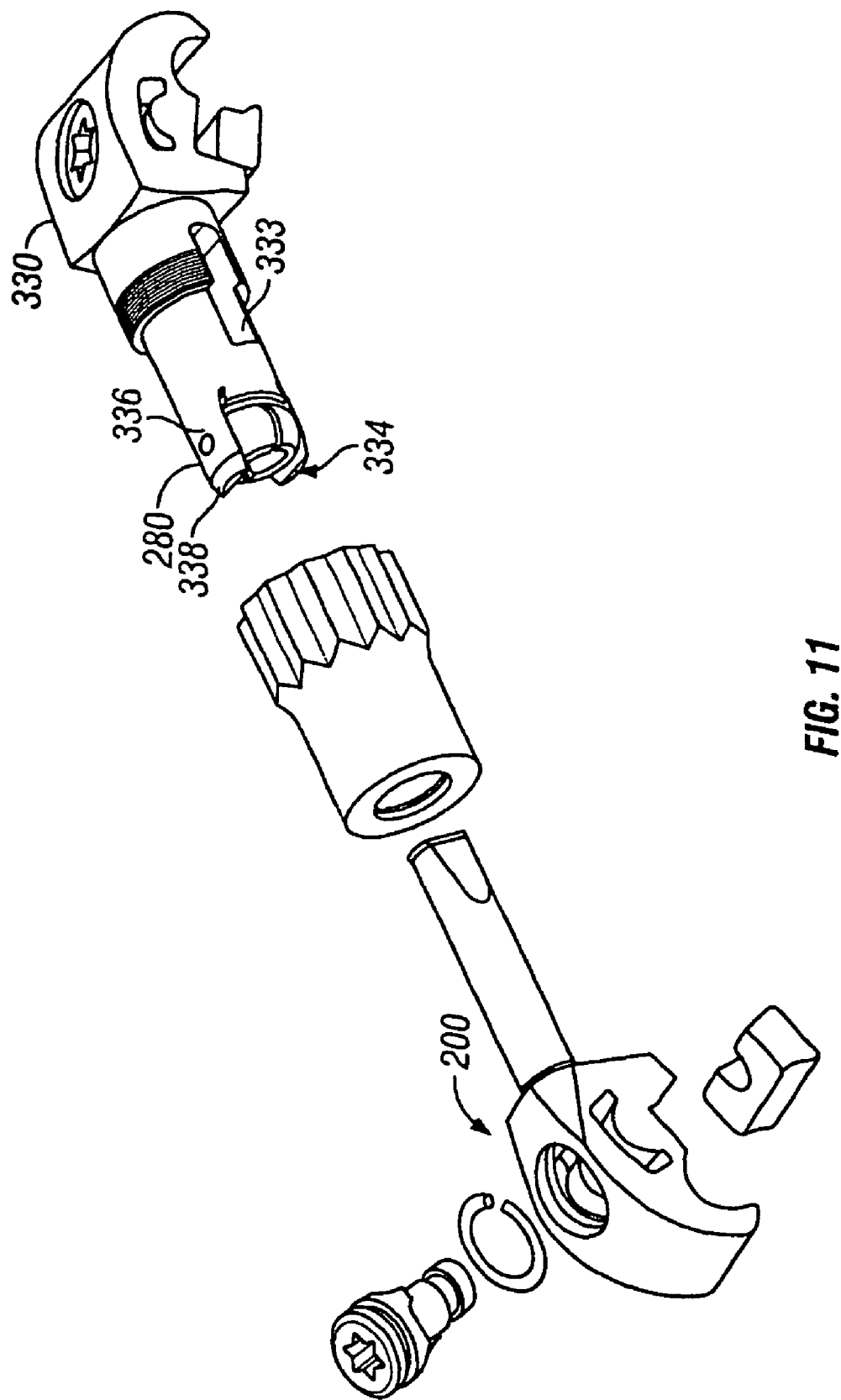
FIG. 11 is an exploded perspective view of a second embodiment of a crosslink member of the present invention.

Referring now to FIGS. 11 and 12, an alternative form of the female connector 330 is provided. The female connector 330 may be utilized with the cross rod connector 200 and sleeve 250, as described above. The female connector 330 has a cavity 332 which receives a clamp device 350 and the cross rod 220, as well as a terminal end 334 for holding the clamp device 350. The clamp device 350 includes an inner cylindrical surface 354 for receiving and mating with the outer surface 222 of the cross rod 220 in the above-described manner.

The terminal end 334 of the female connector 330 includes at least one or, preferably, a pair of deflectable flanges 336, each of which preferably having a chamfered tip 338. Alternatively, the tip 338 may be an edge. When the sleeve 250 is tightened on the female connector 330, as the manner described above for the female connector 202, the shoulder 256 of the sleeve 250 contacts the chamfered tip 338 to compress the clamp device 350 on the cross rod 220.

Figure 13:
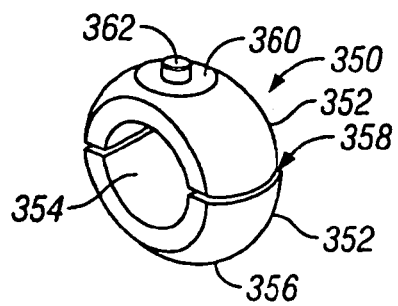
FIG. 13 is a perspective view of a first embodiment of a clamp device of the embodiment of FIG. 11.

As depicted in FIGS. 11 and 13, the clamp device 350 may include two partial or half-ring sections 352, each having an outer curved surface 356. When the cross rod 220 is inserted, the half-ring sections 352 deflect apart to permit the ridge 224 to pass through. A small gap 358 is provided between the half-ring sections 352 so that, when the sleeve 250 compresses the flanges 336, the half-ring sections 352 are similarly compressed to secure the cross rod 220.

As can be seen in FIG. 13, the half-ring sections 352 include a surface 360 for contacting an inside surface 340 of the flanges 336. Preferably, the surfaces 360, 340 include surface structure (not shown) that provide a more secure interface between the surfaces 360, 340. The surface 360 of the half-ring sections 352 includes a post 362, and the flange 336 includes a receptacle, such as a bore 342, for receiving the post 362. Alternatively, the post 362 may be split, spring-like portions that are deflected inward when inserted in the bore 342 and expand when terminal ends of the portions extend through or reach a wider portion of the bore 342. The half-ring sections 352 are permitted to pivot around the post 362, in the manner the clamp device 240 pivots. The surfaces 360, 340 allow the clamp 350 to pivot around an axis and, generally, limits the pivoting motion to a single plane. The receptacle may be a cylindrical bore 342, as depicted, through the flange 336, may be an oversized bore (not shown), or may be a frusta conical bore (not shown) such that the post 362 may also pivot slightly relative to the bore so that the alignment of the half-ring sections 352 relative to the cross rod 220 is unchanged when the flanges 336 are deflected by the sleeve 250. As an alternative, the surfaces 340 of the flanges 336 may be angled to provide optimum compression on the cross rod 220 when the flanges 336 are deflected by being compressed. As a further alternative, the flanges 336 may have posts such as described for the half-ring sections received by bores in the half-ring sections such as described for the flanges.

The half-ring sections 352 may be inserted between the flanges 336 in a manner that requires the flanges 336 to deflect outward so the post 362 may be received in the bore 342. Each half-ring section 352 may then be retained in the flanges 336 as the opposing half-ring section 352 prevents the half-ring section 352 from inadvertently falling out of the flanges 336. It may be desirable to secure further the half-ring sections 352 by, for instance, deforming or swaging an end portion of the post 362 that extends through the bore 342, such as like a rivet that permits rotation of the post 362 within the bore 342. In addition, the assembly of the crosslink 10 having the cross rod 220 between the half-ring sections 352 from falling out of the flanges 336.

As discussed above, the clamp device 240 has an outer curved surface 314 so it remains in contact with and is positioned by the terminal edge 236 of the cavity 230 when pivoted. In contrast, the clamp device 350 has an outer curved surface 356 that is not designed to maintain contact with the inner surface 252 of the sleeve 250, instead being shaped to permit the pivoting of the clamp device 350 without being restricted by interference from the inner surface 252 of the sleeve 250. However, the outer curved surface 356 may, nonetheless, contact and slide against the inner surface 252 of the sleeve 250.

Figure 14:
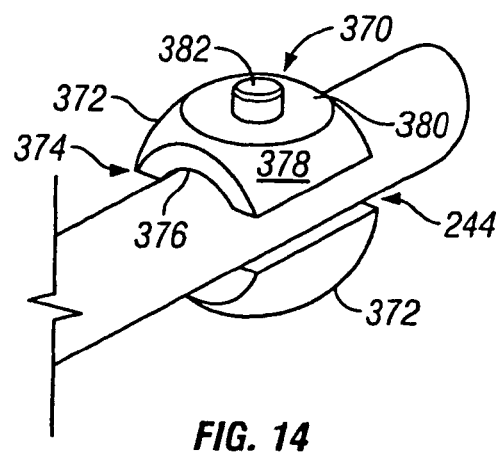
FIG. 14 is a perspective view of a second embodiment of a clamp device of the embodiment of FIG. 11.

As depicted in FIG. 14, an alternative clamp device 370 for use with the female connector 330 may be provided. The clamp 370 has two opposed halves 372 with a gap 374 therebetween, each half 372 having with an inner cylindrical surface 376, an outer curved surface 378, a surface 380 meeting with the inside surface 340 of the flanges 336, and a post 382 received by the bore 342 of the flange 336. The halves 372 operate in the same manner as described above for the clamp 350. However, the gap 374 is larger and retention means, such as swaging the post 382, are preferably utilized to prevent the halves 372 from inadvertently falling out. As compared to the clamp device 350, the clamp device 370 reduces the material required for the clamp device 370 and provides greater clearance between the clamp device 370 and the inner surface 256 of the sleeve 250.

Figure 15:
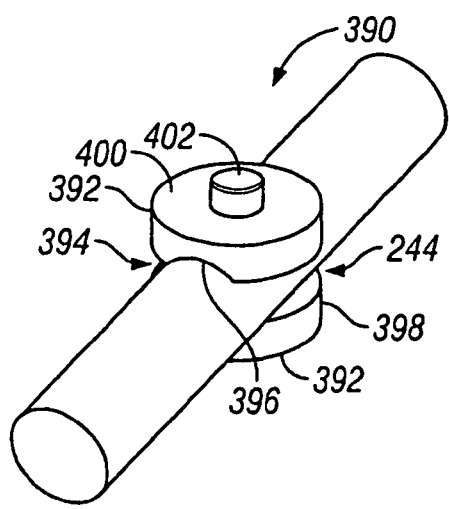
FIG. 15 is a perspective view of a third embodiment of a clamp device of the embodiment of FIG. 11.

FIG. 15 shows further alternative clamp device 390 for use with the female connector 330. The clamp 390 has two opposed halves 392 with a gap 394 therebetween, each half 392 having with an inner cylindrical surface 396, an outer cylindrical surface 398, a surface 400 meeting with the inside surface 340 of the flanges 336, and a post 402 received by the bore 342 of the flange 336. The halves 392 operate in the same manner as described above for the clamps 350, 370. Again, the gap 394 is larger and retention means, such as swaging the post 402, are preferably utilized to prevent the halves 392 from inadvertently falling out. Additionally, the outer cylindrical surface 398 has minimal contact with the inside surface 252 of the sleeve 250. Again, comparing the clamp device 390 to the clamp devices 350, 370, the clamp device 390 requires less material while providing additional clearance between the clamp device 390 and the inner surface 256 of the sleeve 250.

It should be noted that other embodiments of the clamp device 350 maybe utilized. Preferably, the clamp device used is permitted to pivot without being restricted by abutting the inner surface 252 of the sleeve 250. Preferably, any other embodiment may be clamped by compression. Preferably, the clamp device has a cylindrical inner surface for mating with and securing the cross rod 220.

As discussed, the cross rod 220 of the cross rod connector 200 is received in the cavity 230, 332 of the female connector 202, 330, and the cross rod connector 200 may be pivoted relative to the female connector 202, 330, as shown in FIGS. 16 and 17. When the cross rod 220 pivots from side to side, as has been described, contact between the cross rod 220 and any structure limits the angular sweep of the pivoting motion. The range of pivoting preferably includes a sweep of at least 20°, that is, 10° in either direction from the axis 20X. Accordingly, the cavity 230, 332 is provided with side windows 231, 333 to avoid structure which the cross rod 220 may otherwise contact. In addition, the cross rod 220 includes bevels 228 in the outer cylindrical surface 222. Therefore, the cross rod 220 may pivot from side to side with minimal interference, and may pivot with minimal protrusion, if any, from the windows 231, 333 of the female connector 202, 330. Furthermore, the size of the female connector 202, 230 is minimized while allowing the desired sweep of the pivoting cross rod 220.

As one of skill would readily appreciate and understand, the amount of pivot sweep of the cross rod 220 within the cavity 230, 332 of the female connector 202, 330 depends on the relative dimensions of the cross rod 220, the sleeve 250, the inner cavity 230, 332, and the size of the window 231, 333. A person of skill would further appreciate the optimization of these dimensions to produce a desired pivot sweep without sacrificing strength and while balancing the overall size of the crosslink 10.

As can be seen, the central connection portion 14 of the crosslink 10 provides three degrees or manners of adjustment. The amount of the cross rod 220 of the cross rod connector 200 that is inserted in the female connector 202, 330 may be adjusted so that the length of the crosslink 10 may be adjusted according to the distance between the spinal rods 30 to which the crosslink 10 are mounted. The cross rod 220 is secured in a clamp device 240,350 which is pivotable within the female connector 202, 330, thereby allowing the cross rod connector 200 to pivot relative to the female connector 202, 300 and according to the convergence or divergence of the spinal rods 30. Furthermore, the cross rod 220 has a cylindrical outer surface 222 and the clamp device 240, 350 has a cylindrical surface 242, 352 mating with the outer surface 222 of the cross rod 220 so that the cross rod 220 may rotate within the clamp device 240, 350, thereby permitting the cross rod connector 200 and female connector 202, 330 to rotate relative to each other so the crosslink 10 maybe secured to spinal rods 30 whose central axes are twisted or rotated relative to each other. Alternatively, the cross rod 220 may have a non-cylindrical surface received by an inner surface of the clamp device 240, where the clamp device 240 is rotatable within the female connector 202 such that cross rod connector 200 may rotate relative to the female connector. As a further alternative, a bottom surface 233 of the cavity 231 (FIG. 8) may be excavated to allow the cross rod 220 to pivot thereinto, thus providing a further manner of adjustment.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A connecting end for a connecting member for securing spinal rods mounted to spinal vertebrae, the connecting end comprising: a body having a bore extending therethough along a bore axis thereof; a locking member for locking the spinal rod with the locking member being configured to form a spinal rod seat with locked and unlocked positions; and a cam member received in the bore and having a lower end portion projecting beyond the bore with the lower end portion being connected to the locking member outside the bore, the cam member being operable to be rotatable against a cam surface of the body for moving the locking member from the unlocked position to the locked position in an axial direction toward the body and to secure the locking member against the spinal rod.

2. The connecting end of claim 1 wherein the body has an arcuate surface for seating against the spinal rod.

3. The connecting end of claim 1 wherein the locking member seat has an arcuate face such that the arcuate face is secured against the spinal rod when in the locked position.

4. The connecting end of claim 1 further including a spring retention member for biasing the locking member to be held in the unlocked position prior to rotation of the cam member to move the locking member to the locked position.

5. The connecting end of claim 4 wherein the spring retention member is compressed when the locking member is moved to a locked position.

6. The connecting end of claim 1 wherein the bore includes a pair of arcuate camming surfaces for camming against the cam member.

7. A connecting end for a connecting member for securing spinal rods mounted to spinal vertebrae, the connecting end comprising: a locking member for locking the spinal rod such that the locking member forms a spinal rod seat with locked and unlocked positions; a cam member connected to the locking member and rotatable against a cam surface of the connecting end for moving the locking member between the unlocked and locked positions and to secure the locking member against the spinal rod, a spring retention member for biasing the locking member in the unlocked position wherein the spring retention member is compressed when the locking member is moved to a locked position, the spring retention member is a split ring located around the cam member, and the ring is compressed when the locking member is moved to a locked position.

8. A connecting end for a connecting member for securing spinal rods mounted to spinal vertebrae, the connecting end comprising: a locking member for locking the spinal rod such that the locking member forms a spinal rod seat with locked and unlocked positions; and a cam member connected to the locking member and rotatable against a cam surface of the connecting end for moving the locking member between the unlocked and locked positions and to secure the locking member against the spinal rod, wherein the cam member has a recess, and the locking member is secured in the recess of the cam member such that the cam member and locking member may rotate relative to each other.

9. The connecting end of claim 8 wherein the recess is an annular channel.

10. A connecting member for securing spinal rods mounted to spinal vertebrae, the connecting member comprising: a pair of connecting ends each having an arcuate surface and a locking member for seating the connecting member on a pair of spinal rods; and a central span including: a cross rod having a central longitudinal axis and being connected to one connecting end; a rod receiving member having a central longitudinal axis and being connected to the other connecting end, the rod receiving member including an internal cavity for receiving the cross rod with the internal cavity axially elongated to extend along the rod receiving member central longitudinal axis; a clamp device for clamping against the cross rod at least partially received in the rod receiving member; and a sleeve disposed about the rod receiving member outside the internal cavity thereof with the rod receiving member having external threads and the sleeve having internal threads threaded to the rod receiving member external threads so that the clamp device is clamped against the cross rod upon rotation of the sleeve around the central longitudinal axis of the rod receiving member to advance the sleeve therealong.

11. The connecting member of claim 10 wherein the internal cavity of the rod receiving member receives the cross rod such that the cross rod may be adjustably inserted in the cavity for varying the length of the connecting member, the cross rod may be adjustably rotated in the rod receiving member around a longitudinal axis of the cross rod, and the cross rod may be pivoted relative to the rod receiving member.

12. The connecting member of claim 10 wherein the cross rod includes a protrusion for retaining the cross rod within the rod receiving member.

13. The connecting member of claim 10 wherein the sleeve includes an internal structure that imparts a compression force on the clamp device for securing the cross rod.

14. The connecting member of claim 13 wherein the rod receiving member includes a terminal surface for limiting the position of the clamp device.

15. A connecting member for securing spinal rods mounted to spinal vertebrae, the connecting member comprising: a pair of connecting ends each having an arcuate surface and a locking member for seating the connecting member on a pair of spinal rods; and a central span including: a cross rod having a central longitudinal axis and being connected to one connecting end; a rod receiving member having a central longitudinal axis and being connected to the other connecting end, the rod receiving member including an internal cavity for receiving the cross rod; a clamp device for clamping against the cross rod received in the rod receiving member; and a sleeve disposed about the rod receiving member and the clamp device for clamping the clamp device against the cross rod upon rotation of the sleeve around the central longitudinal axis of the rod receiving member, wherein the internal cavity of the rod receiving member receives the cross rod such that the cross rod may be adjustably inserted in the cavity for varying the length of the connecting member, the cross rod may be adjustably rotated in the rod receiving member around a longitudinal axis of the cross rod, and the cross rod may be pivoted relative to the rod receiving member, and wherein the clamp device may pivot to permit pivoting of the cross rod.

16. The connecting member of claim 15 wherein the clamp device includes an inner surface for mating with the external surface of the cross rod.

17. The connecting member of claim 16 wherein with at least a portion of the inner surface of the clamp device is arcuate for mating with the external surface of the cross rod, and the cross rod may be rotatably adjusted relative to the clamp device.

18. A connecting member for securing spinal rods mounted to spinal vertebrae, the connecting member comprising: a pair of connecting ends each having an arcuate surface and a locking member for seating the connecting member on a pair of spinal rods; and a central span including: a cross rod having a central longitudinal axis and being connected to one connecting end; a rod receiving member having a central longitudinal axis and being connected to the other connecting end, the rod receiving member including an internal cavity for receiving the cross rod; a clamp device for clamping against the cross rod received in the rod receiving member; and a sleeve disposed about the rod receiving member and the clamp device for clamping the clamp device against the cross rod upon rotation of the sleeve around the central longitudinal axis of the rod receiving member, wherein the sleeve includes an internal structure that imparts a compression force on the clamp device for securing the cross rod, the rod receiving member includes a terminal surface for limiting the position of the clamp device, and the clamp device is compressed between the terminal surface of the rod receiving member and the internal structure of the sleeve to secure the cross rod.

19. The connecting member of claim 14 wherein the internal structure of the sleeve contacts the clamp device directly.

20. A connecting member for securing spinal rods mounted to spinal vertebrae, the connecting member comprising: a pair of connecting ends each having an arcuate surface and a locking member for seating the connecting member on a pair of spinal rods; and a central span including: a cross rod having a central longitudinal axis and being connected to one connecting end; a rod receiving member having a central longitudinal axis and being connected to the other connecting end, the rod receiving member including an internal cavity for receiving the cross rod; a clamp device for clamping against the cross rod received in the rod receiving member; and a sleeve disposed about the rod receiving member and the clamp device for clamping the clamp device against the cross rod upon rotation of the sleeve around the central longitudinal axis of the rod receiving member, wherein the sleeve includes an internal structure that imparts a compression force on the clamp device for securing the cross rod, the rod receiving member includes a terminal surface for limiting the position of the clamp device, and the internal structure of the sleeve that contacts the clamp device includes a shoulder portion.

21. A connecting member for securing spinal rods mounted to spinal vertebrae, the connecting member comprising: a pair of connecting ends each having an arcuate surface and a locking member for seating the connecting member on a pair of spinal rods; and a central span including: a cross rod having a central longitudinal axis and being connected to one connecting end; a rod receiving member having a central longitudinal axis and being connected to the other connecting end, the rod receiving member including an internal cavity for receiving the cross rod; a clamp device for clamping against the cross rod received in the rod receiving member; and a sleeve disposed about the rod receiving member and the clamp device for clamping the clamp device against the cross rod upon rotation of the sleeve around the central longitudinal axis of the rod receiving member, wherein the sleeve includes an internal structure that imparts a compression force on the clamp device for securing the cross rod, the rod receiving member includes a terminal surface for limiting the position of the clamp device, and the rod receiving member includes a pair of flanges extending about at least a portion of the clamp device, and the internal structure of the sleeve contacts and compresses the flanges to compress the clamp device for securing the cross rod.

22. The connecting member of claim 21 wherein at least one flange and the clamp device are joined by a post and receptacle, the receptacle receiving and holding the post, and the post and receptacle providing a pivot axis for the clamp device so the clamp device and cross rod may pivot within the rod receiving member.

23. The connecting member of claim 22 wherein each flange includes a terminal surface mating with the internal surface of the sleeve to compress the clamp device.

24. A connecting member for securing spinal rods mounted to spinal vertebrae, the connecting member comprising: a pair of connecting ends each having an arcuate surface and a locking member for seating the connecting member on a pair of spinal rods; and a central span including: a cross rod being connected to one connecting end; a rod receiving member being connected to the other connecting end, the rod receiving member including an internal cavity for receiving the cross rod; a clamp device for clamping against the cross rod when received in the rod receiving member; a sleeve extending about the rod receiving member outside the internal cavity thereof and being operable for clamping the clamp device against the cross rod; and side openings in the rod receiving member on either side of the cavity that are covered by the sleeve, wherein the cross rod is pivotal relative to the rod receiving member to extend out from the cavity through either one of the side opening while staying covered outside of the cavity by the sleeve.

25. The connecting member of claim 24 wherein the cross rod has a central longitudinal axis, and the rod receiving member has a central longitudinal axis.

26. The connecting member of claim 25 wherein the lateral surfaces of the cross rod are beveled towards the central longitudinal axis of the cross rod at an end of the cross rod.

27. The connecting member of claim 24 wherein the cross rod may be pivoted to a position such that the cross rod is protruding from one of the side openings.

* * * * *

UNITED STATES PATENT AND TRADEMARK OFFICE
CERTIFICATE OF CORRECTION

PATENT NO.         : 7,927,355 B2                                         Page 1 of 1
APPLICATION NO.    : 11/408629
DATED              : April 19, 2011
INVENTOR(S)        : Berrevoets et al.

It is certified that error appears in the above-identified patent and that said Letters Patent is hereby corrected as shown below:

On the Title Page:

On page 1, Column 1, under "Related U.S. Application Data", Delete "(63) Continuation of application No. PCT/US2004/034897, filed on Oct. 21, 2004" and insert in its place the following: Item --(63) Continuation of International Application PCT/US2004/034897, filed October 21, 2004, which is a continuation of US Application No. 10/692,460, filed October 22, 2003, now US Patent No. 7,744,633, which are hereby incorporated herein by reference in their entirety.--.

Claim 1, column 13, line 16, delete "therethough" and insert --therethrough--.

Signed and Sealed this
Second Day of October, 2012

David J. Kappos
*Director of the United States Patent and Trademark Office*